United States Patent [19]

Collen

[11] 4,346,029

[45] Aug. 24, 1982

[54] ANTIPLASMIN AND ANTISERUM

[75] Inventor: Désiré J. Collen, Winksele, Belgium

[73] Assignee: Leuven Research & Development V.Z.W., Louvain, Belgium

[21] Appl. No.: 5,590

[22] Filed: Jan. 22, 1979

Related U.S. Application Data

[62] Division of Ser. No. 775,462, Mar. 8, 1977, Pat. No. 4,198,335.

[30] Foreign Application Priority Data

Mar. 18, 1976 [NL] Netherlands .......................... 7602846

[51] Int. Cl.$^3$ ...................... A61K 39/395; C07G 7/00
[52] U.S. Cl. ................................. 260/112 B; 424/85; 424/101
[58] Field of Search ............... 260/112 B; 424/85, 101

[56] References Cited

U.S. PATENT DOCUMENTS 3,504,083  3/1970  Philpot .................................. 424/101
3,808,124  4/1974  Dziobkowski et al. ......... 260/112 B
3,943,245  3/1976  Silverstein ........................... 424/101

OTHER PUBLICATIONS

Collen et al., *Thrombosis Research*, vol. 7, No. 1, Jul., 1975, pp. 245-249.

*Primary Examiner*—Howard E. Schain
*Attorney, Agent, or Firm*—Lewis H. Eslinger

[57] ABSTRACT

A newly isolated constituent of human blood plasma, called antiplasmin, is disclosed together with its isolation method. Further, the invention relates to antiplasmin, a newly isolated constituent of the human blood plasma and to its method of isolation. Further, an antiplasmin-antiserum together with its preparation and utilization, and a method of determining antiplasmin in blood samples are disclosed.

3 Claims, No Drawings

ANTIPLASMIN AND ANTISERUM

This is a division of application Ser. No. 775,462, filed Mar. 8, 1977, now U.S. Pat. No. 4,198,335, issued 4/15/80.

The invention relates to a recently found protein with antiplasminic effect from human blood plasma as well as an antiserum against it and methods of production and application of these matters.

It is known that in the human blood plasma there occur various proteins which play a part in the coagulation of blood. These proteins may be classified into two groups, namely on the one hand proteins of the actual blood coagulation system with fibrin as final product and, on the other hand the proteins of the fibrinolytic system with fibrin breakdown products as final products. These two systems are opposite and complementary.

Each protein which constitutes a factor of the blood coagulation or fibrinolytic system has the property that it can be modified from an inactive form or precursory form to an active form in which the activation reaction may be accelerated by catalysts and may be inhibited by inhibitors. Furthermore, all activation reactions together have been found to form a continuous chain of reactions, the so-called coagulation respectively fibrinolytic cascade, the product of each activation reaction appearing as an enzyme in the following reaction. So, the last step but one in the fibrinolytic cascade consists of a modification of plasminogen into plasmin, which plasmin may than appear as an enzyme in the final step, namely the modification of fibrin into fibrin breakdown products.

The part of the plasmin in the fibrinolytic system has been researched extensively in vitro and at least 5 plasma proteins have been found which may serve as inhibitor for plasmin, namely $\alpha_2$-macroglobulin, $\alpha_1$-antitrypsin, inter-$\alpha$-trypsin-inhibitor, antithrombin III and $C_1$-esterase-inhibitor. Generally it is assumed that, in fact, only two of these proteins are important for the inhibition of plasmin, namely the quick reacting $\alpha_2$-macroglobulin and the slower reacting $\alpha_1$-antitrypsin.

Experiments made by applicant, as stated in U.S. patent application Ser. No. 723,187, have revealed that the enzymes of the blood coagulation system and of the fibrinolytic system developed by activation in a specific step of the cascade are neutralized rather quickly in the blood plasma by the available inhibitors with formation of enzyme-inhibitor-complexes and that these complexes with the aid of physical-chemical expedients can be isolated from the activated plasma. It has also been revealed that, in the case of plasmin, the complexes formed deviate from what might be expected on the strength of the common knowledge referred to above.

Namely, when plasminogen marked with radioactive iodine is added to blood plasma and the fibrinolytic system of the blood plasma is subsequently activated with streptoquinase or uroquinase (known enzymes) so that the available plasminogen is modified into plasmin, two kinds of radioactive complexes can be separated from the activated plasma by chromatography. The one complex can be identified as a complex of plasmin with the known inhibitor $\alpha_2$-macroglobulin, the other is found to be a complex of plasmin with a protein unknown up to now which differs from the five inhibitors mentioned above and which has been mentioned "antiplasmin" (abbreviated AP).

In the course of experiments which conducted to the invention, isolation of the antiplasmin in its free state from blood plasma has been successful. This antiplasmin appears to be a protein with a molecular weight of around 55.000 and an electrophoretic migration speed in agarosegel in the order of $\alpha_2$-globulins, whilst immunochemical reactions with antisera against $\alpha_2$-macroglobulin, $\alpha_1$-antitrypsin, antithrombin III, inter-$\alpha$-trypsin-inhibitor, $C_1$-esterase-inhibitor and antichymotrypsin are absent.

The invention, therefore, provides in the first place the new protein antiplasmin which is characterized by the properties just mentioned. Furthermore, it provides a method of producing this protein and possibilities for its application.

On principle, antiplasmin can be produced from fresh human blood plasma in various manners. However, as long as no physical-chemical method is available, antiplasmin may be best isolated in the immunochemical way. By preference this is done by immunoadsorption to insolubilized antibodies against antiplasmin. If, for instance, such antibodies are insolubilized by coupling them to 6-aminohexyl-Sepharose, an adsorption column can be built up thereof which is particularly suitable for absorbing antiplasmin. If subsequently fresh human blood plasma is made flow over the column, particularly the available antiplasmin from the blood plasma will be bonded to the insolubilized antibodies. Later on, this bonded antiplasmin can be eluted from the column with a suitable agent such as, for instance, a solution of cyanate of potassium or ammoniumthiocyanate, or a solution of glycin-HCl. By gelfiltration, for instance on Ultrogel AcA 44 or a similar agent, a purified antiplasmin may subsequently be obtained.

The isolated and purified antiplasmin may be applied for making antisera and antibodies. Furthermore, a therapeutical application to patients who consume much antiplasmin is conceivable, such as patients with intervenous blood coagulation or during thrombolytic therapy.

The antibodies needed for preparing antiplasmin may be obtained by purification of an antiserum generated against plasmin-antiplasmin-complex in such a way that substantially the specific antiplasmin antibodies are left. In this connection, it has to be considered that the P-AP-antiserum generally comprises antibodies against plasmin and plasminogen, against antiplasmin, against P-AP-complex and possibly also contaminating antibodies against all kinds of other antigens. Purification may be carried out, for instance, by incubating the fresh antiserum with fresh blood plasma (for the purpose of removing almost all contaminating antibodies and purified plasminogen (for the purpose of removing antibodies against plasminogen and plasmin) and then removing the precipitate obtained. The amount of fresh blood plasma should be sufficient for the removal of all contaminating antibodies but insufficient for the removal of the antibodies against antiplasmin from the antiserum. This amount may vary strongly dependent on the experimental animal used for generating the antiserum, but according to the examples outlined below, an amount of 0.5 to 2% in relation to the fresh antiserum will suffice as a rule. The amount of purified plasminogen should suffice to remove all available antibodies against plasminogen and practically all available antibodies against plasmin from the antiserum. Also this amount depends on the experimental animal used in the preparation of the antiserum, be it that in the following examples an amount of 45 to 55 milligrams per liter of antiserum has been found to be sufficient. A purified antiserum substantially still comprising antibodies against antiplasmin with specific antibodies against P-AP-complex in addition, is then obtained. This purified antiserum, either or not after further purification, may then be used for making insolubilized antibodies.

Purification of the P-AP-antiserum may also be carried out with fresh blood plasma alone, but in that case rather large amounts of blood plasma, for instance about 100%, is needed for removing the antibodies against plasminogen. Mostly this will lead to exhaustion of the antibodies against antiplasmin. Moreover, purification may also be carried out by incubation of the fresh antiserum with AP-free human blood plasma and purified plasminogen for which there is no limit to the amount of blood plasma. Finally, it is conceivable that the specific antibodies are obtained by purification of an antiserum against antiplasmin in one of the ways mentioned. These methods will be described later on.

In the second place, the invention provides an antiserum comprising antibodies against antiplasmin and it also indicates some methods for its production and applications.

On principle, the antiplasmin-antiserum may be prepared in various manners starting from a P-AP-complex or from the antiplasmin itself.

In the former method of preparation, first an antiserum against plasmin-antiplasmin-complex is generated, for instance by injecting experimental animals with this complex, drawing blood regularly and collecting the blood serum from the blood drawn. This antiserum, which generally comprises antibodies against plasminogen and plasmin, against antiplasmin, against P-AP-complex and contaminating antibodies against all kinds of other antigens, is subsequently purified in such a way that substantially the specific antibodies against antiplasmin are left. This may be done, for instance, in the manner outlined before by incubating the fresh antiserum with fresh blood plasma and purified plasminogen in amounts suitable therefor. A purified antiserum comprising substantially antibodies against antiplasmin, with an insignificant amount of antibodies against P-AP-complex in addition, is then obtained.

Purification of the antiserum generated against P-AP-complex may also be done by incubation with AP-free human blood plasma and purified plasminogen. The amount of AP-free blood plasma should be sufficient for removing practically all contaminating antibodies but, in view of the absence of antiplasmin, it is not bound to a limit. The amount of purified plasminogen should suffice for the removal of all antibodies against plasminogen and practically all antibodies against plasmin. The AP-free blood plasma may be obtained by submitting fresh human blood plasma to immunoadsorption on a column of insolubilized AP-antibodies; for this purpose use may be made of the filtrate left in the insulation of antiplasmin from fresh blood plasma. Of course, this method is only applicable after first the extraction of antiplasmin from blood plasma has been started.

Purification of the P-AP-antiserum might also be done with fresh or AP-free human blood plasma alone, but this has the disadvantage that a rather large amount of blood plasma is required.

Another possibility is that the AP-antiserum is prepared direct with antiplasmin. In that case, first an antiserum is generated in the customary way, for instance by injecting experimental animals with the antiplasmin, drawing blood from the animals regularly and collecting the serum from the blood drawn. The antiserum obtained comprises antibodies against antiplasmin, but also contaminating antibodies against all kinds of other antigens. It should be purified in such a way that substantially the antibodies against antiplasmin are left which may be carried out, for instance, by incubation with fresh or AP-free blood plasma and removal of the precipitate obtained. The amount of blood plasma to be added should be sufficient for the removal of practically all contaminating antibodies, nevertheless retaining the specific AP-antibodies as much as possible. An antiserum still comprising antibodies against antiplasmin only is obtained.

Of course, the antiserum purified in the described ways may then still be submitted to further methods of purification, for instance by precipitating, separating and resuspending the globulin fraction of the antiserum.

The AP-antiserum according to the invention may be applied for the preparation of insolubilized antibodies and may serve also as a reagent in the method of determination to be described later on.

If the antiserum is applied for making insolubilized antibodies, the antibodies from the purified antiserum may be bonded to 6-hexyl-Seraphose as described above. In their turn, the insolubilized antibodies may serve for the adsorption of antiplasmin from fresh blood plasma.

The invention provides furthermore a method of determination of antiplasmin in human blood plasma. Such a method of determination may be useful for demonstrating deviations in the antiplasmin content of the blood. Such deviations are caused by, for instance, abnormal synthesis of antiplasmin, like with patients with serious liver diseases, or otherwise excessive consumption of antiplasmin, like in situations of intravenous coagulation or thrombolytic therapy.

The method of determination according to the invention consists in that the presence of antiplasmin in blood plasma is determined by immuno-electrophoresis or other manner. By preference, the immuno-electrophoresis method of Laurell is used for this purpose. In this method, an agarosegel in its fluid state is mixed homogeneously with an antiserum (in this case antiserum against antiplasmin) and poured out on a plate to a layer of 1 mm thickness. Then an electric field is laid across the plate in one direction, due to which part of the proteins will migrate from the plasma samples to the positive pole. The migrating proteins meet the antibodies from the plate due to which their speed is inhibited and finally precipitin lines are formed. From the formation of the precipitin lines, the presence of the protein searched (in this case antiplasmin) in the blood samples can be concluded. The amount of antiplasmin may be calculated approximately from the migration distance to the precipitation line and the surface of the migration peak. In this manner both a qualitative and a quantitative analysis is possible.

As a reagent for the method of determination described, only an antiserum against antiplasmin is needed, as described in the foregoing.

Instead of the immunoelectrophoretic method, also an immunochemical method might be applied, for instance an agglutination-inhibiting test with the aid of an antiserum and a special latex- or bloodcell-reagent, or a direct agglutination test with a latex- or bloodcell-reagent only. The antiserum needed for this purpose is provided by the invention, whilst the latex- or bloodcell-reagent may be made in a simple manner with the aid of antiplasmin or antiplasmin-antiserum. Furthermore, various other methods of determination are possible, such as radial immunodiffusion, radio-immunoassay, etc.

The following examples serve to illustrate the invention without limiting it. The preparation of the plasmin-antiplasmin-complex, however, has been taken from U.S. patent application Ser. No. 723,187 and does not as such form part of the present invention.

EXAMPLE I

Isolation of P-AP-complex from blood plasma

The P-AP-complex together with P-$\alpha_2$M, was isolated from blood plasma activated with streptokinase or urokinase to which traces of radioactive marked plasminogen were added. Insulation was carried out by affinity chromatography on lysin-agarose and gelfiltration on Sephadex G-200.

Starting materials

As starting material bloodbank plasma from normal donors caught on ACD-anti-coagulant, was taken. As activators, streptokinase (Kabikinase of Kabi AB, Stockholm) and urokinase (of Abbott, North Chicago, Ill., USA) were used. The radioactive marked plasminogen was prepared as follows: human plasminogen was obtained from fresh frozen plasma obtained by affinity chromatography on lysin-agarose, gelfiltration on Sephadex G-150 and chromatography on DEAE-Sephadex, as described in D. Collen's thesis "Plasminogen and prothrombin metabolism in man", University of Leuven, Belgium, 1974. From this strongly purified material, two principal forms of plasminogen were separated by affinity chromatography on lysin-agarose. The two forms identified as plasminogen $A_1$ (first peak) and plasminogen $A_2$ (second peak), were marked respectively with $^{125}$I and $^{131}$I according to McFarlane, Nature, (London) 182, 53, 1958.

Isolation

To portions of 1 liter of blood plasma, traces of $^{125}$I plasminogen-$A_1$ and $^{131}$I plasminogen-$A_2$ were added, after which the plasma was activated by the addition of 250 or 500 CTA units of activator per ml of blood plasma and 30 minutes incubation at room temperature. Subsequently, the activated plasma was carried through a lysin-agarose column of 2.5×45 cm at a speed of 50–70 ml per hour, this column being equilibrated with 0.1 M of phosphate buffer of pH 7.5. Not-adsorbed protein was removed by washing with the equilibration buffer. In these circumstances, about 90% of the radioactivity was retained by the column. Elution was carried out with a linear gradient comprising 500 ml of 0.1 M phosphate of pH 7.5 as a starting buffer and 500 ml of 0.1 M phosphate, 0.013 M of epsilon-aminocaproic acid, with pH 7.5, as an end-buffer. The elution profile of the radioactivity comprised 6 peaks which, in the order of elution, were identified as follows: (1) $^{125}$I-plasmin $A_1$-$\alpha_2$-macroglobulin, (2) $^{131}$I-plasmin $A_2$-$\alpha_2$-macroglobulin, (3) $^{125}$I-plasmin $A_1$-antiplasmin, (4) and (5) $^{131}$I-plasmin $A_2$-antiplasmin and remaining $^{125}$I-plasminogen $A_1$ and (6) remaining $^{131}$I-plasminogen $A_2$.

Various fractions of the chromatogram were concentrated by ultrafiltration and further purified by gel filtration on Sephadex G-200, the sequence of elution being: (1) $^{125}$I-plasmin $A_1$- 2-macroglobulin complex and $^{131}$I-plasmin $A_2$- 2-macroglobulin complex in the empty volume of the column, (2) $^{125}$I-plasmin $A_1$-antiplasmin and $^{131}$I-plasmin $A_2$-antiplasmin obtained from plasma by chromatography just before the 7S globulin peak, and (3) $^{125}$I plasminogen $A_1$ and $^{131}$I-plasminogen $A_2$, eluted in the valley between globulins and albumins of plasma.

The fractions of various Sephadex G-200 columns were later on combined to three large fractions corresponding to the groups, 1, 2 and 3 just mentioned. These fractions were dialyzed against distilled water and lyofilized. The average proceeds of eight insulation tests of 1 liter of blood plasma each were: 14.5 units optical density at 280 nm per 100 ml of plasma in the first fraction (henceforth identified as P-$\alpha_2$M) and 7.3 units per 100 ml of plasma in the second fraction (henceforth identified as P-AP).

Identification

During gel-electrophoresis of P-$\alpha_2$M on SDS-polyacrylamide, a protein band was observed which almost did not migrate in the gel (molecular weight exceeding 400.000). Upon repetition of this experiment, after reduction with dithiothreitol (DTT) various bands were observed the most important of which has a molecular weight of about 95.000. Immunoelectrophoresis according to Laurell in a gel with $\alpha_2$-macroglobulin-antiserum confirmed the identity of the P-$\alpha_2$ M-complex. The complex did not react with antisera against $\alpha_1$-antitrypsin, $C_1$-inhibitor, antothrombin III and inter-$\alpha$-trypsin-inhibitor.

During gel-electrophoresis of P-AP on polyacrylamide, two protein bands with a molecular weight of about 120.000 and about 140.000 were obtained. After reduction with DTT, two protein bands with molecular weights of around 65.000 and around 15.000 were observed. No precipitin formation was obtained by immunoelectrophoresis according to Laurell in gels comprising antisera against $\alpha_1$-antitrypsin, $\alpha_2$-macroglobulin, $C_1$-esterase inhibitor, inter-$\alpha$-trypsin inhibitor, antithrombin III and $\alpha_2$-antichymotrypsin. On the other hand, in this experiment a reaction was obtained with antiserum generated against the P-AP complex which was absorbed with purified plasminogen. This indicates that P-AP comprises a complex between plasmin and a plasma protein with antiplasmin properties not identified before which has further been named antiplasmin.

EXAMPLE II

Preparation of P-AP-antiserum

Rabbits were immunized with plasmin-antiplasmin complex. For this purpose, the complex was solved in a 0.15 M kitchen-salt solution to a concentration of 2 mg per ml and mixed with 1 ml of complete Freund adjuvant. Per rabbit 1 ml of this mixture was injected divided on the soles of the feet, the subcutaneous tissue in the neck and the thigh muscles. Three times after that, each time at an interval of 1 or 2 weeks, an equal amount of antigen was administered mixed with incomplete Freund adjuvant and divided on the subcutaneous and the intramuscular way. Commencing one week after the fourth injection, 30–80 ml of blood was taken twice per week by punction of the ear arteries. The serum of 3 or 4 consecutive blood-takings was each time combined and further worked up jointly.

EXAMPLE III

Purification of P-AP-antiserum

A P-AP-antiserum obtained according to Example II was purified in three steps, namely incubation with fresh blood plasma and plasminogen, precipitation and resuspension of the globulin fraction and affinity chromatography on insolubilized P-AP complex so as to retain substantially a solution of antibodies against antiplasmin.

1. To 25 ml of antiserum of Example II 2% of fresh human blood plasma and 5.0 mg of purified plasminogen (0.2 mg per ml of serum) was added. After 30 minutes incubation at room temperature the precipitate obtained was removed by separation.

2. The fluid left was diluted 1:5 with a buffer solution (0.1 M NaCl, 0.05 disodiumhydrophosphate, pH 7.0), after which the globulin fraction was precipitated at 4° C. by addition of a 100% saturated ammoniumsulphate solution to a total degree of saturation of 40%. After 120 minutes stirring at 4° C., the precipitate obtained was separated off, solved to the original volume in the above mentioned buffer solution, dialyzed for 2 hours against a tris-buffer (0.1 M tris-HCl, pH 8.6) or bicarbonate buffer (0.1 M $NaCO_3$, pH 8.1) for removing ammonium- and sulphate ions, and finally cleared by separation.

3. An insolubilized P-AP-complex was prepared by coupling purified P-AP-complex to agarose activated by cyanbromide. For this purpose, 75 ml of agarose A5M (sedimented volume) was solved in water, mixed with an aqueous solution of 10 g of CNBr and cooled down so as to obtain an activated gel. This gel was washed with a cold coupling buffer (0.1 M $NaHCO_3$, 0.5 M NaCl, pH 8.0) and added to a solution of 75 units O.D. of purified P-AP-complex (according to Example I) in 100 ml of coupling buffer. After 2 hours mixing at room temperature and 1 night standing at 4° C., the gel was washed with small amounts of coupling buffer and mixed with an ethanolamine solution (0.1 M ethanolamine in coupling buffer, pH 8.0) in a ratio of 50:50. After 1 hour standing at room temperature the gel was washed with a large amount of coupling buffer.

A portion of the insolubilized P-AP-complex was poured into a chromatographic column of 0.9×10 cm. Then the product of step 2 (the resuspended globulin fraction) was carried over the column at a speed of 10 ml/cm$^2$/hour. The column was washed out with a phosphate buffer (0.1 M NaCl, 0.05 phosphate, pH 7.5) after which the bonded antibodies were eluted with a 3 M ammonium-thiocyanate solution.

The eluent was dialyzed against the phosphate buffer and concentrated by vacuum dialysis. A purified antiserum comprising substantially specific antibodies against antiplasmin with antibodies against neo-antigens in the P-AP-complex was obtained (compare U.S. patent application Ser. No. 723,187).

EXAMPLE IV

Isolation of antiplasmin from blood plasma

Antiplasmin was isolated from human blood plasma by immunoadsorption on insolubilized AP-antibodies and further purified by gelfiltration on Ultrogel AcA 44.

The insolubilized antibodies were obtained by bonding the purified antiserum of Example III (in which, therefore, the specific antibodies against antiplasmin were present) to 6-aminohexyl-Sepharose with the aid of glutaaraldehyde, according to the method of Cambiaso et al (Immunochemistry, 12, 273-278, 1975). For the antibodies from 25 ml of original antiserum 7.5 ml of 6-aminohexyl-Sepharose was used.

Preparation of 6-aminohexyl-Sepharose 100 ml of sedimented Sepharose 4B was suspended in 100 ml of icy-cold water after washing with distilled water, after which 30 g of solid CNBr was added whilst stirring. By addition of 8 M NaOH the pH was raised to 11. The total was stirred in an ice-bath for 5–10 minutes and at room temperature for 5–10 minutes, so that the total reaction time was 10–20 minutes. The activated gel was washed with 1 liter of cooled buffer solution (0.1 M $Na_2CO_3$, pH 10), after which 100 ml of cooled 4% aqueous solution of hexamethylendiamin (brought to pH 10 with HCl) was added to the activated gel. The total was stirred for 16 hours at 4° C. and then washed extensively with distilled water for removing the surplus of hexamethylendiamin. The gel was stored at 4° C. as a 50% suspension in water.

Activation with glutaraldehyde

The gel obtained from 6-aminohexyl-Sepharose was first washed 10× with a buffer solution (0.1 M $Na_2CO_3$, pH 8.5), after which stirring, a mixture of 7 ml of $Na_2CO_3$-buffer and 1 ml of 25% glutaraldehyde was added to 3 ml of sedimented gel. After 15 minutes stirring at room temperature a yellowish-green colour was formed. Then the gel was washed 5× with 20 ml of $Na_2CO_3$-buffer for removing the non-bonded glutaraldehyde.

Insolubilization of AP-antibodies

The purified antiserum of Example III (originating from 25 ml of original antiserum) was added to the activated 6-aminohexyl-Sepharose-gel (7.5 ml). After 15 minutes stirring at room temperature the gel was washed with 20 ml of $Na_2CO_3$-buffer. By measuring the optical density in the filtrate it was found that 93% of the AP-antibodies was bonded to the gel.

Immunoadsorption

A portion of the insolubilized antibodies was poured into a chromatographic column of 0.9×10 cm, after which these antibodies were suitable for adsorbing antiplasmin from fresh blood plasma. The antibodies emanating from 25 ml of original antiserum could bond the antiplasmin from 10 ml of fresh plasma.

Fresh human blood plasma was carried over the column of insolubilized antibodies at a speed of 10 ml/cm$^2$/hour. In these circumstances, all the antiplasmin was bonded. Not-bonded protein was washed away carefully, first with a phosphate buffer (0.1 M NaCl, 0.05 M disodium hydrophosphate, pH 7.5) and then with another phosphate buffer (1.0 M NaCl, 0.05 disodiumhydrophosphate, pH 7.5). Subsequently the bonded antiplasmin was eluted with 3 M ammoniumthiocyanate solution.

The eluent was dialyzed against a buffer solution (0.1 M NaCl, 0.05 M phosphate, pH 7.5), concentrated by vacuum dialysis and purified by gelfiltration on Ultrogel AcA 44. The antiplasmin-containing fractions of the gelfiltration column were combined by vacuum dialysis.

Identification

For this purpose, the crossed immunoelectrophoresis test in agarose according to Clarke and Freeman (Clin., Sci., 35, 403, 1968) was applied. In the course of the performance of this test with (a) the isolated antiplasmin of this example against (b) a purified AP-antiserum of Example III, a clear precipitin line in the $\alpha_2$-globulin position was obtained. Performance of this test with (a) the antiplasmin of this example against (b) an antiserum generated against complete human blood serum, shew a clear precipitin line in the albumen position and two weak precipitin lines elsewhere. Upon electrophoresis in SDS-polyacrylamidegel two bands were obtained with a molecular weight of around 68.000 (albumin) and around 55.000 (antiplasmin). The colour intensity of both bands was practically equivalent. No immunochemical reactions were obtained with antisera against $\alpha_2$-macroglobulin, $\alpha_1$-antitrypsin, antithrombin III, inter-$\alpha$-trypsin inhibitor, $C_1$-esterase-inhibitor and $\alpha_1$-antichymotrypsin.

EXAMPLE V

Purification of P-AP-antiserum

A P-AP-antiserum obtained according to Example II was purified by incubation with AP-free human blood plasma and purified plasminogen and removal of the precipitate obtained so as to retain substantially a solution of antibodies against antiplasmin.

For the AP-free blood plasma the remaining fluid of Example IV was used, i.e. a blood plasma free of antiplasmin by carrying over a column of insolubilized AP-antibodies.

The purified plasminogen was prepared according to the method described in D. Collen's thesis "Plasminogen and prothrombin metabolism in man", University of Louvain, Belgium, 1974.

400 ml of antiserum obtained by repeated blood-drawing from two rabbits immunized with P-AP-complex and stored at $-20°$ C. in the presence of 0.1% of sodiumazide was melted and clarified by separation. During the test of crossed immunoelectrophoresis with (a) fresh human blood plasma against (b) the said antiserum, two intense precipitin lines were observed in the $\alpha_2$-globulin position (antiplasmin) and the $\beta_2$-globulin position (plasminogen) and, moreover, two scarcely noticeable weak precipitin lines elsewhere.

To the antiserum 0.5% of AP-free blood plasma was added as also a solution of 7 mg of purified plasminogen in 3 ml physiologic salt solution. The total was stirred at room temperature for 2 hours and at 4° C. for 1 night and then clarified by separation. In crossed immunoelectrophoresis against fresh human blood plasma an increase of the surface under the precipitin curve was observed in the $\beta_2$-position (indicating a decrease of the antibodies against plasminogen) and the other weak precipitin lines had vanished. The formation of precipitin with the component in the $\alpha_2$-position had remained unchanged.

Again 7 mg of purified plasminogen was added to the solution and the total was stirred during the night and then clarified. In crossed immunoelectrophoresis still a small amount of antibodies against the $\beta_2$-component was found to be present.

Subsequently incubation with 5 mg of purified plasminogen was done once more. After separation, the solution at electroimmunodiffusion and crossed immunoelectrophoresis was found to comprise only antibodies against antiplasmin.

The endproduct was clarified by ultraseparation for one hour at 19000 rpm (Beckman L2-65B separator, rotor type 19).

A purified antiserum comprising substantially antibodies against antiplasmin was obtained.

EXAMPLE VI

Purification of P-AP-antiserum (repetition)

At crossed immunoelectrophoresis against fresh human blood plasma, 1020 ml of antiserum obtained by repeatedly drawing blood from 5 rabbits immunized with P-AP-complex, also shew two precipitin lines in the $\beta_2$-position (plasminogen) and the $\alpha_2$-position, with another three weak precipitin lines elsewhere. This antiserum was purified by incubation with 1% of antiplasmin-free blood plasma (obtained from Example IV) and 15 mg of plasminogen, followed up by twice incubating with each time 15 mg of purified plasminogen and once incubating with 10 mg of purified plasminogen.

The endproduct was clarified by ultraseparation for 1 hour at 19000 rpm (Beckman L2-65B separator, rotor type 19).

A purified antiserum comprising substantially antibodies against antiplasmin was obtained.

EXAMPLE VII

Determination of antiplasmin in blood plasma

The antiplasmin content in human blood plasma was determined with the Laurell electroimmunodiffusion method. For this purpose, the blood plasma of patients with various diseases was used, the plasma of a group of 38 sound persons serving as a check range.

In the course of the performance of the experiment, an agarosegel in its fluid state (56°-60° C.) was mixed homogeneously with a portion of the AP-antiserum obtained in Example VI, and then poured out on a plate to a gel-layer of 1 mm thickness. After cooling down, samples of the blood plasma to be examined were brought into little holes of the gel-layer, and an electric field was laid in one direction on the plate. On the plate precipitin lines were formed from which a value for the antiplasmin content could be calculated. The values obtained, expressed as percentage of the value for a plasmapool of 20 sound persons, are recorded in the following table. In this table, always an average value and also the standard deviation from the average, as well as the signification of the difference with the check-range is given.

| Identification | Number | Average | Standard deviation | P |
|---|---|---|---|---|
| Check range | 38 | 101.3 | 15.3 | |
| Liver cirrhosis | 8 | 74.4 | 27.4 | <0.01 |
| Hepatitis | 8 | 86.0 | 14.0 | <0.02 |
| Kidney insufficiences | 11 | 98.9 | 9.3 | |
| Myeloproliferation | 11 | 85.0 | 29.5 | >0.05 |
| Malignant condition | 20 | 101.7 | 22.4 | |
| Intravenous coagulation | 6 | 30.8 | 15.0 | <0.01 |

From the table it is evident that the AP-content in the blood plasma of patients with liver cirrhosis has decreased significantly and also of patients with hepatitis, though to a lesser degree. Seeing that, in the case of these patients, no indication was found of increased consumption but, on the other hand, of imperfect protein synthesis in the liver, this decrease is the result of decreased production. In the case of patients with intervenous coagulation, the decrease is obviously attributable to increased consumption. As regards other serious diseases without impediments in the protein synthesis or abnormally increased breakdown, the antiplasmin content is normal.

With the same method the antiplasmin content was determined in cases where the coagulation system or fibrinolytic system was activated in vivo for therapeutical purposes. After activation of the fibrinolytic system with streptokinase a strong decrease of the antiplasmin content to below 25% was observed, which was followed by a normalisation after termination of the treatment in 1-3 days.

After defibrination with reptilase, a reactive fibrinolysis was observed with decrease of the antiplasmin content attributable to consumption.

What I claim is:

1. A method of preparing an antiserum against antiplasmin, comprising the steps of:
   (a) generating an antiserum against plasmin-antiplasmin complex, said generated antiserum containing a plurality of antibodies including antibodies against antiplasmin;
   (b) selectively purifying said generated antiserum by removing antibodies other than antibodies against antiplasmin by incubating said antiserum with antiplasmin-free human blood plasma and purified plasminogen and removing the precipitate thus formed.

2. A method of preparing an antiserum against antiplasmin, comprising the steps of:
   (a) generating an antiserum against plasmin-antiplasmin complex, said generated antiserum containing a plurality of antibodies including antibodies against antiplasmin;
   (b) selectively purifying said generated antiserum by removing antibodies other than antibodies against antiplasmin by incubating said antiserum with antiplasmin-free blood plasma and removing the precipitate thus formed.

3. A method of generating an antiserum against antiplasmin comprising the steps of:
   (a) generating an antiserum directly against antiplasmin, said generated antiserum containing a plurality of antibodies including antibodies against antiplasmin; and
   (b) selectively purifying said generated antiserum by removing antobodies other than antibodies against antiplasmin by incubating said antiserum with antiplasmin-free blood plasma and removing the precipitate thus formed.

* * * * *